United States Patent [19]

Friesen et al.

[11] Patent Number: 4,678,278

[45] Date of Patent: Jul. 7, 1987

[54] SIGHT TUBE FOR MONITORING OF FLUIDS

[75] Inventors: Albert D. Friesen; Walter F. Grassler, both of Winnipeg, Canada

[73] Assignee: The Winnipeg Rh Institute Inc., Winnipeg, Canada

[21] Appl. No.: 677,860

[22] Filed: Dec. 4, 1984

[30] Foreign Application Priority Data

Aug. 16, 1984 [CA] Canada ............................ 461169

[51] Int. Cl.⁴ .............................................. G02B 5/00
[52] U.S. Cl. ..................................... 350/319; 356/246
[58] Field of Search .................. 350/319, 312; 356/39, 356/42, 44, 239-244, 246; 250/573, 576, 577

[56] References Cited

U.S. PATENT DOCUMENTS

| | | | |
|---|---|---|---|
| 4,088,448 | 5/1978 | Lilja et al. ........................ | 356/246 |
| 4,221,470 | 9/1980 | Weeks .............................. | 350/319 |
| 4,441,365 | 4/1984 | Schulz et al. ..................... | 350/319 |
| 4,444,498 | 4/1984 | Heinemann ....................... | 356/246 |

Primary Examiner—John K. Corbin
Assistant Examiner—Loha Ben
Attorney, Agent, or Firm—Burns, Doane, Swecker & Mathis

[57] ABSTRACT

A sight tube for ultraviolet monitoring of liquid and capable of handling industrial scale flow rates for example 40 gallons (180 liters) per minute in which the shape is especially designed to allow oppositely disposed windows, through which the ultraviolet light passes, to be relatively close together. The sight tube has an interior the central section of which has a flat sided portion adjacent and parallel to the windows, the flat sided portion being flanked by two side portions which are thicker than said flat sided portion, the tube having cylindrical end sections joined to the central section by intermediate sections which provide gradual transitions between the section shapes.

3 Claims, 4 Drawing Figures

SIGHT TUBE FOR MONITORING OF FLUIDS

The present invention relates to a sight tube for monitoring fluids and especially a sight tube for ultraviolet monitoring of liquids at relatively high flow rates.

Ultraviolet monitoring equipment is available for liquids flowing from research apparatus at relatively low flow rates, usually well below 1 gallon (4.55 liters, in British Imperial System) per minute. However, there has developed a need for ultraviolet monitoring of liquids at much higher flow rates. For example, liquid chromatographic separation of proteins is becoming an important part of the biotech industry, and one important step in such separations is the monitoring of the effluent for protein. Since proteins absorb ultraviolet U.V.) light, the most common technique for monitoring the proteins eluted from a chromatographic process is to measure the U.V. absorption of the effluent. U.V. monitoring equipment for this purpose needs a sight tube or flow tube capable of handling the entire stream of column effluent at a flow rate which may be as high as 40 gallons (180 liters) per minute. The design must be compatible with clean-in-place systems, that is there should be no cracks or crevices in which product can lodge and from which bacteria cannot be removed during automatic cleaning operations. Furthermore, the flow tube should be compatible with available U.V. cells or at least the light path should be relatively short, for example 10 cm. If the light path is too large then either a powerful light source is required or a very sensitive U.V. light detector. This requirement means that conventional sight tubes cannot be merely scaled up to meet the required flow.

The present invention provides a sight tube in which the thickness of fluid being viewed is small in relation to the overall cross sectional flow area, and also one in which the fluid can flow without undue turbulence and without creating a pressure drop at the point of U.V. monitoring.

In accordance with the present invention, a sight tube, of the kind having windows at opposite sides and by means of which a flowing fluid may be monitored, has an interior characterized by a central section with a flat-sided portion lying between and parallel to the windows, which flat-sided portion isflanked by two side portions which are thicker than the central portion in planes perpendicular to a medial plane of the central portion, the tube also having end sections of circular cross section and intermediate sections connecting the end sections to the central section which intermediate sections provide smooth transitions from the ends to the central sections.

The invention will be further described by way of example with reference to the accompanying drawings showing a preferred embodiment, in which.

Figures 1, 2, 3, 4:
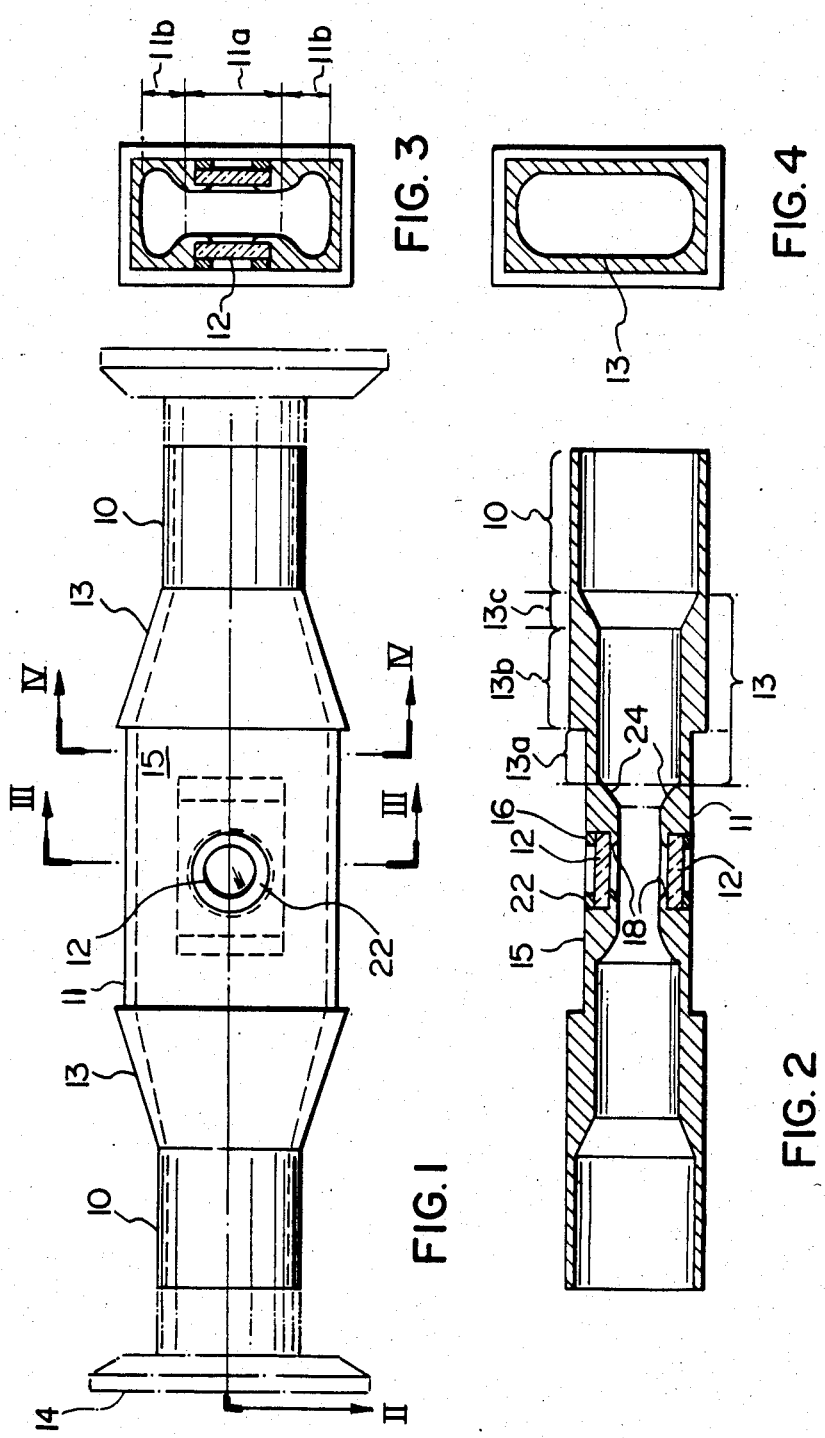
FIG. 1 shows a side elevation of a sight tube and also illustrates a type of sanitary fitting attached to the ends of the sight tube.
FIG. 2 shows a longitudinal section on lines II—II of FIG. 1.
FIG. 3 shows a cross sectional view on lines III—III of FIG. 1.
FIG. 4 shows a cross sectional view on lines IV—IV of FIG. 1.

The sight tube, which may for example be formed from stainless steel, is an elongated hollow body with cylindrical end sections 10, a central section 11 in which are mounted oppositely disposed windows 12, and two intermediate sections 13 providing a gradual transition between sections 10 and 11. On the outer ends of end sections 10 there may be welded santiary fittings 14 known as "tri-clamp" fittings which are attachable to fittings on associated piping.

The central section 11 has opposed side walls 15 with outwardly opening recesses 16 concentrically surrounding circular apertures 18. Each recess 16 is fitted with a circular quartz window 12 held in place by a brass ring 22 having a fine thread which engages a threaded outer part of the recess. The windows are thus oppositely disposed and in practice may be about 10 cm apart, and allow U.V. light to be passed through the tube and monitored on the other side.

As shown in FIG. 3, the central section 11 has a central, flat sided portion 11a which is between and parallel to the windows 12, and this section is flanked by side portions 11b which are thicker than portion 11a in planes perpendicular to the medial plane of portion 11a, and which are rounded in cross sectional shape, and which bulge outwards on each side beyond the planes of the inner faces of windows 12. The resulting cross sectional shape of the central section is similar to a dumbell.

The intermediate sections 13 each include a first part 13a which is generally parallel sided and has an oblong internal shape with rounded corners as shown in FIG. 4; this has the same width as the interior of the central section and the same thickness as parts 11b of the central section. The longer sides of the interior of part 13a, are connected to the adjacent parts of the central section by sloping shoulders 24 seen in FIG. 2. The main part 13b of each intermediate section has an interior which retains the same general form and thickness as part 13a but reduces in width to the internal diameter of the end section 10. A final part 13c of the intermediate section has internal walls which expand laterally (again as seen in FIG. 2) to the circular form of the end section 10.

It will be seen that the design has a generally smooth interior which avoids sharp discontinuities, and that the interior cross sectional area of the central section is similar to the cross sectional area of the end sections. The use of the bar bell shape in the central section allows the windows to be relatively close together while giving a fairly large total flow area, at the same time avoiding the amount of lateral flow which would be required if the whole central area were to be uniformly flattened. The shape ensures that the liquid flow in the central section will have uniform product consistency similar to the product at the end sections so that the analysis obtained by the U.V. absorption will be representative of the U.V. absorption of the total product flow. Also, the design minimizes sharp corners or crevices in which bacteria could accumulate, and all surfaces can be cleaned with automatic flushing systems.

We claim:

1. A sight tube of the kind having windows at opposite sides and by means of which a flowing fluid may be monitored by light passing through the windows, wherein the interior of the tube has a central section with a flat sided portion between and parallel to said windows, said interim having the flat sided portion flanked by two side portions which are thicker than said flat sided portion in planes perpendicular to a medial plane of the flat sided portion, the tube having end sections of circular cross section joined to the central section by intermediate sections which provide gradual transitions from the end sections to the central section.

2. A sight tube according to claim 1 wherein said side portions bulge outwards on each side beyond the planes of the inner faces of the windows.

3. A sight tube according to claim 1 wherein said intermediate sections have a main portion with an interior of oblong cross sectional shape and which reduces in width towards said end sections.

* * * * *

UNITED STATES PATENT AND TRADEMARK OFFICE
CERTIFICATE OF CORRECTION

PATENT NO. : 4,678,278

DATED : July 7, 1987

INVENTOR(S) : Albert D. Friesen; Walter F. Grassler

It is certified that error appears in the above-identified patent and that said Letters Patent is hereby corrected as shown below:

```
Column 1, line 29, change "10 cm." to -- 10 mm. --.

Column 2, line 13, change "10 cm." to -- 10 mm. --;
Column 2, line 64, change "interim" to -- interior --.
```

Signed and Sealed this

Twenty-fifth Day of October, 1988

Attest:

DONALD J. QUIGG

Attesting Officer

Commissioner of Patents and Trademarks